United States Patent
Borsotti et al.

(10) Patent No.: US 9,359,318 B2
(45) Date of Patent: Jun. 7, 2016

(54) PROCESS FOR THE SYNTHESIS OF 2,5-FURANDICARBOXYLIC ACID

(75) Inventors: Giampietro Borsotti, Novara (IT); Francesca Digioia, Novara (IT)

(73) Assignee: Novamont S.p.A., Novara (IT)

( * ) Notice: Subject to any disclaimer, the term of this patent is extended or adjusted under 35 U.S.C. 154(b) by 0 days.

(21) Appl. No.: 13/814,402

(22) PCT Filed: Aug. 4, 2011

(86) PCT No.: PCT/EP2011/063482
§ 371 (c)(1), (2), (4) Date: Feb. 5, 2013

(87) PCT Pub. No.: WO2012/017052
PCT Pub. Date: Feb. 9, 2012

(65) Prior Publication Data
US 2013/0137882 A1    May 30, 2013

(30) Foreign Application Priority Data
Aug. 6, 2010 (IT) .............................. MI2010A1526

(51) Int. Cl.
*C07D 307/30* (2006.01)
*C07D 307/68* (2006.01)
*C07D 307/24* (2006.01)

(52) U.S. Cl.
CPC ............ *C07D 307/30* (2013.01); *C07D 307/24* (2013.01); *C07D 307/68* (2013.01)

(58) Field of Classification Search
CPC ............................ C07D 307/30; C07D 307/68
USPC ......................................................... 549/485
See application file for complete search history.

(56) References Cited

U.S. PATENT DOCUMENTS
4,977,283 A * 12/1990 Leupold et al. ............... 549/484

FOREIGN PATENT DOCUMENTS
FR          2669634 A1    5/1992
WO   WO-2008/054804 A2   5/2008

OTHER PUBLICATIONS

Vinke et al., "On the oxygen tolerance of noble metal catalysts in liquid phase alcohol oxidations: the influence of the support on catalyst deactivation", 1991, Studies in Surface Science and Catalysis, 59(Heterog. Catal. Fine Chem. 2), 385-94, XP009143653.

* cited by examiner

*Primary Examiner* — Golam M M Shameem
*Assistant Examiner* — Raymond Covington
(74) *Attorney, Agent, or Firm* — Polsinelli PC

(57) ABSTRACT

Process for the synthesis of 2,5-furandicarboxylic acid through the oxidation of -hydroxymethylfurfural in a flow of oxygenor a compound containing oxygen, catalyzed by a supported catalyst containing a metal of the platinum group, carried out in aqueous solution in which the pH is maintained higher than 7 and lower than 12 through the addition of a weak base.

20 Claims, No Drawings

PROCESS FOR THE SYNTHESIS OF 2,5-FURANDICARBOXYLIC ACID

CROSS REFERENCE TO RELATED APPLICATIONS

This application is a National Phase filing under 35 U.S.C. §371 of PCT/EP2011/063482 filed on Aug. 4, 2011; and this application claims priority to Application No. MI2010A001526 filed in Italy on Aug. 6, 2010; the entire contents of all are hereby incorporated by reference.

This invention relates to a process for the synthesis of 2,5-furandicarboxylic acid (FDCA) through the oxidation of 5-hydroxymethylfurfural (HMF).

2,5-furandicarboxylic acid is an oxidised derivative of 5-hydroxymethylfurfural which is useful as a monomer in the manufacture of plastics, in particular polyesters. Also, as HMF is in turn obtained from sugars, it is a derivative of raw materials which are widely available in nature.

Processes for the oxidation of HMF through which 2,5-furandicarboxylic acid can be obtained as the main product are known in the literature.

Document U.S. Pat. No. 4,977,283 (Hoechst) describes a method for the oxidation of HMF in the presence of a metal catalyst belonging to the platinum group, carried out in an aqueous environment at a pH of between 6.5 and 8. The patent discloses that by controlling pH it is possible to influence the proportions between the various oxidation products and by-products. According to the information included in the patent, control of pH can be achieved through bases such as sodium or potassium hydroxide, acids or buffer solutions, as a rule maintaining a pH of less than 8.

Patent application US 2008/0103318 (Battelle) describes a method for the oxidation of HMF catalysed by supported platinum. Again in this case emphasis is placed on the variation in selectivity as a function of pH, which must be maintained at a value of not more than 7, possibly through the use of weak bases such as carbonates and bicarbonates. 2,5-furandicarboxylic acid is one of the oxidation products described.

The metal catalysts used in the methods for the oxidation of HMF described above are however subject to poisoning and consequent loss of catalytic activity. This means that although supported catalysts that can be easily recovered are used it is frequently necessary to replace or regenerate the catalyst, adding costs to the already expensive use of precious metals such as platinum.

Patent application FR 2 669 634 provides an example of catalyst recycling to overcome this drawback. The above-mentioned document describes a process for the synthesis of FDCA comprising the oxidation of HMF catalysed by platinum in aqueous medium in a flow of oxygen, in which recycling is possible because the catalyst is enriched with specific quantities of lead.

The process described nevertheless requires use of a considerable quantity of catalyst, which is used in a ratio of between 1:10 and 1:30 by weight with respect to HMF, equivalent to a molar ratio of less than 1:50.

A similar ratio between catalyst and HMF is however necessary in order to achieve a high oxidation yield of HMF to 2,5-furandicarboxylic acid, as will be seen from the data relating to the processes according to the abovementioned documents.

The process for the synthesis of 2,5-furandicarboxylic acid according to this invention has the particular advantage that it provides a high yield of 2,5-furandicarboxylic acid using a limited quantity of catalyst. The latter may also be recycled several times while maintaining its specific catalytic activity.

This invention relates in particular to a process for the selective synthesis of 2,5-furandicarboxylic acid through the oxidation of 5-hydroxymethylfurfural in a flow of oxygen, catalysed by a supported catalyst containing a metal of the platinum group, the said process being carried out in aqueous solution at a weakly basic pH through the addition of a weak base. This process provides for the use of quantities of catalyst of between 1:60 and 1:500, in moles with respect to HMF. It also provides for the possibility of recycling the catalyst several times in the reaction mixture while maintaining the reaction yield above 90%.

With the terms "recycling" and "recycled" is meant that the same catalyst is used more than once to repeat the same process.

It has in fact surprisingly been discovered that the maintenance of a weakly basic pH in the reaction environment, by the addition of a weak base, preserves the catalyst from poisoning. Under the process conditions according to this invention, recycling of the catalyst in fact makes it possible to obtain 2,5-furandicarboxylic acid in high yields. This is the case despite the use of smaller quantities of catalyst in relation to the HMF reagent, confirming that process selectivity is substantial and that catalytic activity is effectively maintained.

The starting material in the process according to this invention is 5-hydroxymethylfurfural (HMF). HMF may be obtained by the dehydration of sugars, in particular hexoses such as fructose and glucose. Said sugars may be obtained by the hydrolysis and possible isomerisation of cellulose or polysaccharides containing biomass. According to a preferred embodiment of the present invention the HMF is thus obtained from cellulose or polysaccharides containing biomass. Cellulose or polysaccharides containing biomass are examples of raw materials which are widely available in nature and as such are a renewable source for HMF.

The dehydration reaction may be performed by many techniques which generally use acid catalysts and may or may not use aqueous and non-aqueous solvents.

The HMF used as the starting material for the process according to the invention may possibly contain by-products from the processing of sugars, polysaccharides or cellulosic biomasses.

In the process according to this invention the oxidation of HMF takes place in aqueous solution and does not require the help of organic solvents in that the pH conditions have the effect that the product of the oxidation reaction present in dissociated form is readily soluble in water, as is HMF. An aqueous solution at HMF concentration up to 30% by weight is advantageously used; HMF concentrations comprised between 0.5 and 20% by weight are preferred, and HMF concentrations comprised between 1 and 10% by weight are even more preferred.

In the process according to the invention the oxidising substance responsible for the oxidation of HMF is oxygen or a compound containing oxygen. Advantageously the reaction is performed by passing a flow of $O_2$ into the reactor.

Advantageously the catalyst used is based on platinum or a metal belonging to the platinum group; the use of platinum or palladium is particularly preferred. This catalyst is advantageously used in supported form. The most suitable materials for providing a support for the said catalyst are carbon or alumina. The supporting material may possibly be in the form of a nanostructure, and contains the catalyst in a quantity which is preferably between 1 and 10% by weight.

In a preferred form of the process according to the invention the catalyst comprises 5% by weight of Pt supported on carbon.

The catalyst used in the process according to this invention is used in small quantities in comparison with the quantity of reagent. Advantageously the molar ratio between HMF and the catalyst metal lies between 60:1 and 500:1, preferably between 80:1 and 350:1, and even more preferably between 100:1 and 250:1.

The catalyst used in the process according to the present invention is advantageously recycled in the reaction mixture at least once, and even more advantageously at least four times, maintaining the reaction yield above 90%.

The 5-hydroxymethylfurfural oxidation reaction is performed at a temperature of between 80 and 120° C., preferably between 90 and 110° C. and more preferably between 90 and 105° C., and at a pressure of between atmospheric pressure and $10*10^5$ Pa, advantageously between $2*10^5$ and $8*10^5$ Pa, more advantageously between $3*10^5$ and $6*10^5$ Pa.

As is known, according to the Brønsted-Lowry theory, weak bases are chemical bases which are not completely protonated in an aqueous solution, thus resulting in a higher concentration of hydrogen ions and in a lower pH compared to strong bases such as NaOH or KOH.

The weak bases whose presence is required for implementing this invention have a small base dissociation constant (Kb), with a $pK_b \geq 1.5$ at 25° C. in a dilute aqueous solution ($\leq 1$ mol/dm$^3$), preferably with a $pK_b \geq 1.8$ and more preferably with a $pK_b \geq 2$. In any case said bases are used in quantities necessary to maintain over the course of the HMF oxidation reaction a pH higher than 7 in the reaction environment, but lower than 12 in order to prevent the occurring of undesired side reactions such as Cannizzaro reactions.

The weak bases according to the invention are preferably selected from: sodium bicarbonate, potassium bicarbonate, sodium carbonate, potassium carbonate, calcium carbonate, magnesium carbonate, calcium hydroxide, magnesium hydroxide, dibasic and tribasic phosphate buffer solutions and their mixtures.

The maintenance of a weakly basic pH in the reaction environment can be achieved either by adding the weak base before starting the HMF oxidation reaction or adding part of the weak base before starting the HMF oxidation reaction and part after said reaction has started.

When the weak base is added before starting the HMF oxidation reaction, the aqueous solution containing HMF and said weak base has advantageously a pH value higher than or equal to 8 and lower than 12, preferably higher than 8.5 and lower than 11. The presence of the weak base maintains a slightly basic reaction environment over the course of the oxidation reaction, an aqueous solution with a pH value higher than 7 and lower than 11 being obtained at the end of the oxidation reaction. Under such conditions it has unexpectedly been found that the catalyst maintains its intrinsic catalytic activity almost unchanged and its re-use makes it possible to selectively produce FDCA with an almost total conversion of HMF. Recycling may be performed many times, obtaining a clear final solution (colourless to slightly yellow) and maintaining a production yield of FDCA of more than 90%.

When part of the weak base is added to the reaction mixture before starting the HMF oxidation reaction and part is added gradually, according to the change in pH, after the HMF oxidation reaction has started, the pH value is advantageously maintained higher than 7 and lower than 11, preferably higher than 8 and lower than or equal to 8.5.

In a preferred embodiment of the invention poorly soluble weak bases are used. By the term "poorly soluble weak bases" are intended weak bases which have solubility in water lower than 20 g/100 g H$_2$O, measured at 20° C. and under $1*10^5$ Pa pressure. Such poorly soluble bases can be advantageously added before starting the reaction and they gradually pass into solution during the reaction, so balancing pH changes due to the production of FDCA and maintaining a slightly basic reaction environment over the course of the oxidation reaction. Examples of preferred poorly soluble weak bases are sodium bicarbonate, calcium and magnesium carbonates, magnesium hydroxides and their mixtures. Particularly preferred is magnesium carbonate hydroxide.

In a preferred embodiment of the invention the process provides for a preliminary stage comprising the preparation of a reaction intermediate through the oxidation of HMF with non-precious-metal catalysts such as for example copper.

Advantageously said intermediate is 5-hydroxymethylfuran-2-carboxylic acid, HMFA. The HMFA obtained through this preliminary stage is easily purified, allowing the oxidation according to the invention to be performed using an intermediate reagent (HMFA) which is purer than the HMF, with a further positive effect on the life and activity of the catalyst.

In this case it is necessary to use a suitable quantity of the weak base to neutralise the acidity of the reaction intermediate.

The 2,5-furandicarboxylic acid produced according to this invention is present in aqueous solution in dissociated form on completion of the oxidation reaction. Once the catalyst has been separated off by means of known techniques FDCA can be obtained in the form of a precipitate by neutralising the aqueous solution.

The process according to the invention can be performed either in batches or continuously.

The process according to the invention will now be described according to the following non-limiting examples.

EXAMPLE 1

0.5 g of catalyst comprising 5% by weight platinum supported on carbon Degussa type F101RA/W, (sold by Sigma-Aldrich; with a water content of 50% w),
50 g of a 2% by weight aqueous solution of HMF (HMF:Pt=123:1),
1.5 g of NaHCO$_3$ were placed in an autoclave fitted with a magnetic stirrer and an inlet with a dip pipe for bubbling in oxygen. The pH value of aqueous solution was of 8.1.

The reactor was heated in an oil bath at 100° C. and maintained at a pressure of $5*10^5$ Pa, while O$_2$ was delivered into it at a flow of 20 L/h.

After 4 hours the conversion of HMF was virtually complete. The colourless aqueous solution containing 2,5-furandicarboxylic acid in dissociated form had a pH value of about 9.

The catalyst was filtered off and washed with water; the aqueous solution was acidified in order to precipitate out the FDCA. The production of FDCA was 95% of theoretical molar yield.

The catalyst recovered by filtration was used again to repeat the reaction in the same way. After the first recycling stage the final solution was still colourless and the production yield of FDCA was again 95% of theoretical, and remained above 90% for the next four recycling stages.

COMPARATIVE EXAMPLE 0.5 g of catalyst comprising 5% by weight platinum supported on carbon (Degussa type F101RA/W), 50 g of a 2% by weight aqueous solution of HMF (HMF: Pt=123:1),
0.7 g of NaHCO$_3$ were placed in the same autoclave as used in Example 1. The pH value of the aqueous solution was 8.

The reactor was heated to 100° C. in an oil bath and held at a pressure of 5*10$^5$ Pa, while O$_2$ was delivered to it at a flow of 20 L/h.

After 5 hours the aqueous solution had a pH value of about 3. The catalyst was filtered off and washed with water. The production yield of FDCA was 70% of theoretical, indicating a significant loss of activity in the catalyst.

EXAMPLE 2

0.50 g of catalyst comprising 5% by weight platinum supported on carbon (Degussa type F101RA/W),
50 g of a 2% by weight aqueous solution of HMF (HMF: Pt=123:1),
0.8 g of magnesium carbonate hydroxide (light, sold by Sigma-Aldrich)

were placed in the same autoclave as used in Example 1. The autoclave was heated in an oil bath at 100° C. and maintained at a pressure of 5*10$^5$ Pa, while O$_2$ was delivered into it at a flow of 20 L/h. After 5 hours the conversion of HMF was virtually complete. The pH value of the reaction solution changed from 10.4 to 8.0.

The catalyst was filtered off and washed with water; the colourless aqueous solution containing 2,5-furandicarboxylic acid in dissociated form was acidified in order to precipitate out the FDCA. The production yield of FDCA was 94% of theoretical.

The catalyst recovered by filtration was used again to repeat the reaction in the same way. After five recycling stage the final solution was slightly yellowish and the production yield of FDCA was again 92% of theoretical, and remained above 90% for the next two recycling stages.

EXAMPLE 3

0.5 g of catalyst comprising 5% by weight platinum supported on carbon (Degussa type F101RA/W),
50 g of a 4% by weight aqueous solution of HMF (HMF: Pt=246:1),
2.7 g of NaHCO$_3$ were placed in the same autoclave as used in Example 1. The pH value of the aqueous solution was of 8.1.

The reaction was carried out as in Example 1. After 4 hours the colourless aqueous solution containing 2,5-furandicarboxylic acid in dissociated form had a pH value of 8.96. The production yield of FDCA was 92% of theoretical.

The catalyst recovered by filtration and washed with water was used again to repeat the reaction in the same way. After the first recycling stage the final solution was still colourless and the production yield of FDCA was again 92% of theoretical, and remained above 90% for the next three recycling stages.

EXAMPLE 4

0.5 g of catalyst comprising 5% by weight platinum supported on carbon (Degussa type F101RA/W),
50 g of water,
2.84 g of hydroxymethylfurancarboxylic acid (HMFA),
3.5 g of NaHCO$_3$ were placed in an autoclave fitted with a magnetic stirrer and an inlet with a dip pipe for bubbling in oxygen. The reactor was heated to 100° C. in an oil bath and held at a pressure of 5*10$^5$ Pa. O$_2$ was delivered to it at a flow of approximately 20 L/h. The pH value of the solution was 8.

After 4 hours the pH value of the aqueous solution was 8.9 and the production yield of FDCA was 96% of theoretical.

Recycling the catalyst and reacting it in the same way provided a production yield of FDCA of 94.5% of theoretical.

The invention claimed is:

1. Process for the synthesis of 2,5-furandicarboxylic acid through the oxidation of 5-hydroxymethylfurfural by an oxidising substance which is oxygen or a compound containing oxygen, catalysed by a supported catalyst containing a metal of the platinum group and being free of lead, carried out in aqueous solution whose pH is maintained higher than 7 and lower than 12 through the addition of a weak base, wherein upon completion of the oxidation reaction said catalyst is separated from said aqueous solution and recycled to a new aqueous solution for the synthesis of 2,5-furandicarboxylic acid.

2. Process according to claim 1 wherein the oxidation of 5-hydroxymethylfurfural is carried out by a flow of oxygen.

3. Process according to claim 1 wherein the weak base is added before starting the 5-hydroxymethylfurfural oxidation reaction, wherein the pH value of the aqueous solution containing 5-hydroxymethylfurfural and said weak base is higher than or equal to 8 and lower than 12, and the pH value of the aqueous solution at the end of the oxidation reaction is higher than 7 and lower than 11.

4. Process according to claim 1 wherein part of the weak base is added to the reaction mixture before starting the 5-hydroxymethylfurfural oxidation reaction and part is gradually added after said reaction has started, and wherein the pH of the aqueous solution is maintained higher than 7 and lower than 11.

5. Process according to claim 1 in which the said weak base is selected from: sodium bicarbonate, potassium bicarbonate, sodium carbonate, potassium carbonate, calcium carbonate, magnesium carbonate, calcium hydroxide, magnesium hydroxide, dibasic and tribasic phosphate buffer solutions and their mixtures.

6. Process according to claim 5 in which the weak base is a poorly soluble weak base.

7. Process according to claim 6 in which said poorly soluble weak base is selected from sodium bicarbonate, calcium and magnesium carbonates, magnesium hydroxides and their mixtures.

8. Process according to claim 1 in which quantities of catalyst metal between 1:60 and 1:500 in moles with respect to 5-hydroxymethylfurfural are used.

9. Process according to claim 1 in which the catalyst is Pt or Pd supported on carbon or alumina.

10. Process according to claim 1 in which the catalyst is recycled at least four times.

11. Process according to claim 1 carried out at a temperature of between 80 and 120° C. and at a pressure of between atmospheric pressure and 10*10$^5$ Pa.

12. Process according to claim 1 comprising a preliminary stage of oxidising 5-hydroxymethylfurfural catalysed by non-precious metals in order to obtain an easily purifiable reaction intermediate, said intermediate being 5-hydroxymethylfuran-2-carboxylic acid.

13. Process according to claim 1 wherein said 5-hydroxymethylfurfural is obtained from cellulose or polysaccharides containing biomass.

14. Process according to claim 2 wherein the weak base is added before starting the 5-hydroxymethylfurfural oxidation reaction, wherein the pH value of the aqueous solution containing 5-hydroxymethylfurfural and said weak base is higher than or equal to 8 and lower than 12, and the pH value of the aqueous solution at the end of the oxidation reaction is higher than 7 and lower than 11.

15. Process according to claim 2 wherein part of the weak base is added to the reaction mixture before starting the 5-hydroxymethylfurfural oxidation reaction and part is gradually added after said reaction has started, and wherein the pH of the aqueous solution is maintained higher than 7 and lower than 11.

16. Process according to claim 2 in which the said weak base is selected from: sodium bicarbonate, potassium bicarbonate, sodium carbonate, potassium carbonate, calcium carbonate, magnesium carbonate, calcium hydroxide, magnesium hydroxide, dibasic and tribasic phosphate buffer solutions and their mixtures.

17. Process according to claim 3 in which the said weak base is selected from: sodium bicarbonate, potassium bicarbonate, sodium carbonate, potassium carbonate, calcium carbonate, magnesium carbonate, calcium hydroxide, magnesium hydroxide, dibasic and tribasic phosphate buffer solutions and their mixtures.

18. Process according to claim 4 in which the said weak base is selected from: sodium bicarbonate, potassium bicarbonate, sodium carbonate, potassium carbonate, calcium carbonate, magnesium carbonate, calcium hydroxide, magnesium hydroxide, dibasic and tribasic phosphate buffer solutions and their mixtures.

19. Process according to claim 2 in which quantities of catalyst metal between 1:60 and 1:500 in moles with respect to 5-hydroxymethylfurfural are used.

20. Process according to claim 1 wherein said catalyst consists of said metal of the platinum group.

* * * * *